United States Patent [19]

Enei et al.

[11] 3,960,661

[45] June 1, 1976

[54] METHOD FOR PRODUCING INOSINE BY FERMENTATION

[75] Inventors: Hitoshi Enei, Zushi; Katsuaki Sato, Kawasaki; Morikatsu Ishii, Chigasaki; Yoshio Hirose, Fujisawa, all of Japan

[73] Assignee: Ajinomoto Co., Inc., Tokyo, Japan

[22] Filed: Mar. 27, 1975

[21] Appl. No.: 562,401

[30] Foreign Application Priority Data
Mar. 30, 1974  Japan.............................. 49-36370

[52] U.S. Cl............................................ 195/28 N
[51] Int. Cl.². ........................................ C12D 13/06

[58] Field of Search ................................. 195/28 N

[56] References Cited
UNITED STATES PATENTS
3,111,459  11/1963  Motozaki et al. ................. 195/28 N

*Primary Examiner*—Alvin E. Tanenholtz
*Attorney, Agent, or Firm*—Cooper, Dunham, Clark, Griffin & Moran

[57] ABSTRACT

Mutant strains of *Bacillus subtilis* which require adenine for growth and are resistant to at least one sulfa drug produce inosine in culture medium.

7 Claims, No Drawings

METHOD FOR PRODUCING INOSINE BY FERMENTATION

The invention relates to the production of inosine by fermentation.

It is known that mutant strains of Bacillus subtilis requiring adenine, or resistant to 8-azaquanine and requiring adenine produce inosine in culture medium. It has now been found that certain newly discovered mutants of the known strains which are resistant to at least one sulfa drug and require adenine for growth, produce higher yields of inosine than the previously known strains.

The mutants can be obtained by exposing cells of the parent strain to mutagenic agents in a conventional manner, for example, by exposing the cells of the parent strain to a solution of 100 – 300 γ/ml N-methyl-N'-nitro-N-nitrosoguanidine for 30 minutes at 30°C. Mutants resistant to sulfa drugs can be isolated from the exposed strains by selecting the strains which can grow in an aqueous medium or an agar medium containing sufficient amounts of a sulfa drug to suppress the growth of the parent strain.

The sulfa drugs to which the mutants employed in the invention are resistant have the following general features and are generally characterized as antagonists to p-aminobenzoic acid.

1. Their molecular structure generally includes a segment having the formula:

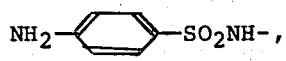

and have anti-microbial action.

2. The anti-microbial action is suppressed by p-aminobenzoic acid.

Typical examples of such sulfa drugs having the foregoing features include sulfapyridine, sulfathiazole, sulfadiazine, sulfaguanidine, sulfamethazine, sulfamerazine, sulfadimethoxine, sulfamethomidine, sulfamethoxypyridazine, sulfaisomidine, sulfisoxazole, acetosulfamine, sulfanylamide, sulfisomerzole, sulfaphenazole, sulfamethizole, sulfaethidole, sulfapyrazine, irgafen and irgamide.

Usually a mutant resistant to one of the sulfa drugs is also resistant to at least one additional sulfa drug.

Mutants of this invention which additionally require, for example, lysine, a vitamine, xanthine, or guanine for nutrition and are resistant to, for example, methionine, methylmethionine sulfonium chloride, methionine sulfoxide, 8-azaguanine, and 6-mercaptopurine, and/or manifest weaker enzyme activity of IMP-dehydrogenase or nucleotidase than the parent strain, generally manifest improved yields of inosine.

The presently preferred inosine producing strains are:

Bacillus subtilis AJ 3721 (FERM-P 2534) (requiring adenine, lysine and thiamine, and resistant to sulfaguanidine)

Bacillus subtilis AJ 3722 (FERM-P 2535) (requiring adenine, lysine and thiamine, and resistant to sulfadiazine)

Bacillus subtilis AJ 3723 (FERM-P 2536) (requiring adenine, and resistant to sulfathiazole)

Bacillus subtilis AJ 3771 (FERM-P 2554) (requiring adenine, resistant to sulfaguanidine and having weaker activity of nucleotidase)

Bacillus subtilis AJ 3772 (FERM-P 2555) (requiring adenine, resistant to sulfaguanidine and having weaker activity to IMP-dehydrogenase)

Bacillus subtilis AJ 3773 (FERM-P 2556) (requiring adenine, and resistant to methionine sulfoxide and sulfaguanidine)

Bacillus subtilis AJ 3774 (FERM-P 2557) (requiring adenine, and resistant to 8-azaguanine and sulfaguanidine).

The mutants are available from the Fermentation Research Institute, Agency of Industrial Science and Technology, at Inage, Chiba-shi, Japan, under the indicated accession numbers.

The media for culturing the microorganisms are conventional except that they contain adenine which is required for growth. They will normally contain sources of carbon, nitrogen, inorganic and, where required, organic nutrients.

Carbohydrates (such as glucose, sucrose, molasses, starch, or starch hydrolyzate), organic acids (such as benzoic acid, acetic acid, propionic acid, higher fatty acids, or fumaric acid), and alcohols (such as ethanol, propanol, sorbitol or glycerine) are the normally preferred carbon sources.

Ammonium salts, nitrate salts, ammonia water, gaseous ammonia and urea can be used as nitrogen sources.

Minor organic nutrients are, for example, amino acids and vitamins and materials containing organic nutrients such as corn steep liquor, soy protein hydrolyzate, beef extract, casein hydrolyzate, or yeast extract.

Cultivation is carried out aerobically, preferably while maintaining a pH of from 5 to 9 and a temperature of 25°C to 40°C.

The following non-limiting examples are given by way of illustration only:

EXAMPLE 1

A medium was prepared to contain, per deciliter, 2.5 g glucose, 0.5 g $NH_4Cl$, 0.4 g $KH_2PO_4$, 0.02 g $MgSO_4 \cdot 7H_2O$, 0.05 g sodium citrate, 0.1 g L-glutamic acid, 1 mg $FeSO_4 \cdot 7H_2O$, 1 mg $MnSO_4 4H_2O$, each 1 γ vitamin $B_1$, $B_2$, and $B_{12}$, 0.2 g casein hydrolyzate (Difico). Three ml batches of the medium with an adjusted pH of 7.0 were mixed with the amounts of the compounds listed in Tables 1–5, and placed in test tubes, and inoculated with a 0.05 ml suspension of the strains listed in the Tables containing $10^6$ cells/ml. Cultivation was carried out at 34°C for 24 hours with shaking. Growth was determined by measuring turbidity of the culture broth.

Cells prepared by the same manner as above were collected by centrifuging, and dried with acetone. IMP-Dehydrogenase and nucleotidase in the dried cells were determined by the methods of Magasanik et al and Heppel et al, respectively. The results are shown in Tables 6 and 7.

Table 1

| Sulfaguanidine added (γ/ml) | AJ 3483 | AJ 3721 | AJ 3771 | AJ 3772 | AJ 3773 | AJ 3774 |
| --- | --- | --- | --- | --- | --- | --- |
| 0 | 100 | 100 | 100 | 100 | 100 | 100 |

Table 1-continued

| Sulfaguanidine added (γ/ml) | AJ 3483 | AJ 3721 | AJ 3771 | AJ 3772 | AJ 3773 | AJ 3774 |
|---|---|---|---|---|---|---|
| 10 | 20 | 98 | 95 | 90 | 96 | 93 |
| 20 | 10 | 85 | 90 | 75 | 92 | 82 |
| 50 | 5 | 80 | 85 | 55 | 84 | 75 |
| 100 | 2 | 32 | 55 | 30 | 45 | 55 |
| 300 | 0 | 18 | 30 | 18 | 12 | 30 |
| 500 | 0 | 5 | 5 | 6 | 6 | 10 |
| 1,000 | 0 | 5 | 2 | 2 | 0 | 8 |

(Note)
AJ 3483 (FERM-P 2117) is an adenine requiring mutant of Bacillus subtilis from which the mutants of this invention were derived.

Table 2

| Sulfadiazine added (γ/ml) | Relative growth (%) | |
|---|---|---|
| | AJ 3483 | AJ 3722 |
| 0 | 100 | 100 |
| 10 | 18 | 98 |
| 20 | 10 | 95 |
| 50 | 6 | 90 |
| 100 | 0 | 85 |
| 300 | 0 | 80 |
| 500 | 0 | 30 |
| 1,000 | 0 | 15 |

Table 3

| Sulfathiazole added (γ/ml) | Relative growth (%) | |
|---|---|---|
| | AJ 3483 | AJ 3723 |
| 0 | 100 | 100 |
| 10 | 35 | 100 |
| 20 | 18 | 88 |
| 50 | 6 | 80 |
| 100 | 0 | 75 |
| 300 | 0 | 50 |
| 500 | 0 | 24 |
| 1,000 | 0 | 7 |

Table 4

| 8-Azaguanine added (γ/ml) | Relative growth (%) | |
|---|---|---|
| | AJ 3483 | AJ 3774 |
| 0 | 100 | 100 |
| 50 | 50 | 100 |
| 100 | 12 | 95 |
| 300 | 0 | 63 |
| 500 | 0 | 40 |
| 1,000 | 0 | 15 |
| 2,000 | 0 | 0 |

Table 5

| Methionine sulfoxide added (γ/ml) | Relative growth (%) | |
|---|---|---|
| | AJ 3483 | AJ 3773 |
| 0 | 100 | 100 |
| 100 | 88 | 100 |
| 1,000 | 32 | 100 |
| 5,000 | 12 | 82 |
| 10,000 | 0 | 53 |
| 20,000 | 0 | 18 |
| 30,000 | 0 | 0 |

Table 6

| | Relative activity of IMP-dehydrogenase |
|---|---|
| AJ 3483 | 100(%) |
| AJ 3772 | 16 |

Table 7

| | Relative activity of nucleotidase |
|---|---|
| AJ 3483 | 100(%) |
| AJ 3771 | 35 |

Fifty milliliter batches of the seed culture medium mentioned below were placed in 500 ml flasks, heated with steam, inoculated with the microorganisms listed in Table 8, and held at 34°C for 16 hours with shaking.

Twenty milliliter batches of the main culture medium mentioned below were placed in 500 ml flasks, inoculated with 15 ml of the seed culture broth mentioned above, and held at 34°C for 72 hours with shaking.

The resulting culture broth contained the amounts of inosine shown in Table 8.

Bacillus subtilis AJ 3774 was cultured in the same manner as mentioned above, and the resultant 1 liter of the culture broth was centrifuged to remove cells, evaporated and cooled to precipitate 7.5 g inosine.

Table 8

| Microorganism | Inosine accumulated (g/dl) |
|---|---|
| AJ 3483 | 0.75 |
| AJ 3721 | 1.45 |
| AJ 3722 | 1.42 |
| AJ 3723 | 1.36 |
| AJ 3771 | 1.64 |
| AJ 3772 | 1.72 |
| AJ 3773 | 1.65 |
| AJ 3774 | 1.42 |

| | Seed culture medium | Main culture medium |
|---|---|---|
| Glucose | 6.0 g/dl | 8.0 g/dl |
| $NH_4Cl$ | 0.3 g/dl | 1.5 g/dl |
| $KH_2PO_4$ | 0.05 g/dl | 0.05 g/dl |
| $MgSO_4 \cdot 7H_2O$ | 0.04 g/dl | 0.04 g/dl |
| $FeSO_4 \cdot 7H_2O$ | — | 1 mg/dl |
| $MnSO_4 \cdot 7H_2O$ | — | 1 mg/dl |
| KCl | — | 2.1 g/dl |
| Soy protein hydrolyzate | 3.2 ml/dl | — |
| RNA | 0.5 g/dl | 0.08 g/dl |
| DL-Methionine | — | 0.03 g/dl |
| L-Lysine | 0.03 g/dl | 0.03 g/dl |
| Thiamine HCl | 200 /l | 5 /l |

| | Seed culture medium | Main culture medium |
|---|---|---|
| CaCO₃ | — | 3 g/dl |
| pH | 7.4 | 7.5 |

What is claimed is:

1. A method for producing inosine, which comprises culturing an inosine-producing mutant of the genus Bacillus, which requires adenine for growth and which is more resistant to at least one sulfa drug than the parent strain from which it is derived and has a resistance at a concentration of 100γ/ml to sulfaguanidine, sulfadiazine or sulfathiazole, under aerobic conditions in an aqueous culture medium until inosine accumulates in the medium, and recovering accumulated inosine from culture medium.

2. A method as set forth in claim 1, in which the mutant is characterized as having less IMP-dehydrogenase activity than the parent strain from which it is derived.

3. A method as set forth in claim 1, in which the mutant is characterized as having less nucleotidase activity than the parent strain from which it is derived.

4. A method as set forth in claim 1, in which the mutant is further characterized as more resistant to methionine sulfoxide or methyl methionine sulfonium chloride than the parent strain from which it is derived.

5. A method as set forth in claim 1, in which the mutant is further characterized as more resistant to 8-azaguanine than the parent strain from which it is derived.

6. A method as set forth in claim 1, in which the mutant is of the species Bacillus subtilis.

7. A method as set forth in claim 1, in which the mutant is Bacillus subtilis FERM-P 2535, Bacillus subtilis FERM-P 2536, Bacillus subtilis FERM-P 2534, Bacillus subtilis FERM-P 2557, Bacillus subtilis FERM-P 2554, Bacillus subtilis FERM-P 2555 or Bacillus subtilis FERM-P 2556.

* * * * *